United States Patent
Nevo et al.

(10) Patent No.: US 6,652,872 B2
(45) Date of Patent: Nov. 25, 2003

(54) SCAFFOLD FORMED OF TISSUE TREATED TO ELIMINATE CELLULAR AND CYTOSOLIC ELEMENTS

(75) Inventors: Zvi Nevo, Herzliya (IL); Dror Robinson, Shimshon (IL)

(73) Assignee: Ramat at Tel Aviv University Ltd., Ramat-Aviv (IL)

(*) Notice: Subject to any disclaimer, the term of this patent is extended or adjusted under 35 U.S.C. 154(b) by 0 days.

(21) Appl. No.: 09/826,389

(22) Filed: Apr. 4, 2001

(65) Prior Publication Data

US 2002/0009805 A1 Jan. 24, 2002

Related U.S. Application Data

(63) Continuation-in-part of application No. 09/345,138, filed on Jul. 6, 1999.

(51) Int. Cl.⁷ .............. A61F 2/00; A61F 2/02; C12N 11/02; C12N 5/04; C12N 5/08
(52) U.S. Cl. ............ 424/423; 424/93.7; 435/177; 435/395; 623/11.11
(58) Field of Search ............... 435/174, 177, 435/395; 424/423, 93.7; 623/11.11

(56) References Cited

U.S. PATENT DOCUMENTS

| | | | |
|---|---|---|---|
| 4,851,354 A | 7/1989 | Winston et al. | 435/284 |
| 4,880,429 A | 11/1989 | Stone | 623/18 |
| 5,108,438 A | 4/1992 | Stone | 623/17 |
| 5,162,114 A | 11/1992 | Kuberasampath et al. | 424/423 |
| 5,843,182 A | 12/1998 | Goldstein | 623/2 |
| 6,037,141 A | 3/2000 | Banes | 435/30 |
| 6,048,964 A | 4/2000 | Lee et al. | 530/350 |
| 6,051,750 A | 4/2000 | Bell | 623/11 |
| 2002/0009805 A1 | 1/2002 | Nevo et al. | 435/366 |

FOREIGN PATENT DOCUMENTS

| | | |
|---|---|---|
| DE | 19808055 | 9/1999 |
| WO | 9214419 | 9/1992 |
| WO | 9721447 | 6/1997 |
| WO | 9749799 | 12/1997 |
| WO | 9814222 | 4/1998 |
| WO | 9822573 | 5/1998 |
| WO | 9952572 | 10/1999 |
| WO | 0041648 | 7/2000 |
| WO | 0102030 | 1/2001 |

OTHER PUBLICATIONS

Mikos, A.G., et al. "Laminated three–dimensional biodegradable foams for use in tissue engineering" Biomaterials, vol. 14, No. 5, (1993).

Hutmacher, D., et al. "Matrix and Carrier materials for Bone Growth Factors: State of . . . Perspective" Stark, G.B., et al. (Eds.) Biological Matrices and Tissue Reconstructions, p. 197–203, (1998).

Kandel, R.A., et al. "Transplantation of Cartilagenous Tissue Generated in vitro into Articular Joint Defects" Art. Cells, Blodd Subs., and Immob. Biotech., vol. 23(5), p. 565–577, (1995).

*Primary Examiner*—David M. Naff
(74) *Attorney, Agent, or Firm*—Ladas & Parry (57) ABSTRACT

A scaffold for use as a growth supportive base for cells and tissue explants is formed of naturally occurring derived connective or skeletal tissue that has been treated for elimination of cellular and cytosolic components comprising DNA, RNA, peptides, lipids and proteoglycans. The treated tissue can be crosslinked and treated for producing a higher porosity such as by mechanical or chemical treatment. Alternatively, the treated tissue is ground to form flakes having a size below 1000μ, and the flakes are attached to each other to provide a scaffold having a porosity of at least 85%. The scaffold may be composed of several single-flake layers arranged on top of the other. The scaffold can be impregnated with cells to form tissue such as epiphysial tissue, and may contain adhesive molecules or growth factors. A prosthesis for implanting can be formed using the scaffold. The scaffold may be composed of fused epiphyses.

16 Claims, 10 Drawing Sheets

SCAFFOLD FORMED OF TISSUE TREATED TO ELIMINATE CELLULAR AND CYTOSOLIC ELEMENTS

This is a continuation-in-part of copending application Ser. No. 09/345,138 filed on Jul. 6, 1999, claims the benefit thereof and incorporates the same by reference.

The invention concerns scaffold matrices for supporting three-dimensional tissues and systems for maintaining three-dimensional viable tissues.

FIELD OF THE INVENTION

The invention concerns scaffold matrices for supporting three-dimensional tissues and systems for maintaining three-dimensional viable tissues.

BACKGROUND OF THE INVENTION

The following publications are believed to be relevant as background of the invention.
1. WO 98/22573
2. U.S. Pat. No. 4,880,429
3. U.S. Pat. No. 4,108,438
4. U.S. Pat. No. 5,843,182
5. Mikos, A. G., Sarakinos, G., Leite, S. M., Vacanti, J. P., and Langer, R., "*Laminated three-dimensional biodegradable foams for use in tissue ingineering*", Biomaterials, 14:323–330, 1993.
6. Hutmacher, D., Kirsch, A., Ackeman, K. L., and Huerzeler, M. B., "*Matrix and carrier materials for bone growth factors—state of the art and future prospectives in:* Stark, G. B., Horch, T, Tancos, E. (eds). *Biological Matrices and Tissue Reconstruction.* Springer Verlag, 1998, pp. 197–203.
7. Kandel, R. A., Chen, H., Clark, J. and Renlund, R., *Transplantation of cartilaginous tissue generated in vitro into articular joint defects.* Biotechnol, 23:565–577, 1995.

Cartilage is a specialized form of connective tissue composed of cells and matrix. The cartilage cells synthesize matrix and become encased in cavities (lacunae) within it. The matrix is composed of fibers embedded in ground substance and endows cartilage with its specialized physico-chemical properties.

Trauma, single or repetitive, and minute imbalance in joint stability are the most known causes of damage and degeneration of articular cartilage, that leads to pain, chronic disability and ultimately to joint failure. The current options for treatment provide temporary improvement of symptoms and function, however, there is no full restoration of joint performance. Prosthetic joint replacement is currently the ultimate and the most commonly employed treatment. Modem biological grafting is the other alternative for resurfacing the damaged joint, but is still imperfect.

A large number of candidate grafts have been studied for enhancing the repair of cartilage defects which include: (i) Osteochondral graft (autografts or allografts); (ii) Intact cartilage grafts; (iii) Growth plate; (iv) Isolated allogeneic chondrocytes; (v) Cultured autologous chondrocytes (dedifferentiated) (vi) Periosteum; (vii) Perichondrium; (viii) Bone marrow mesenchymal derived cells and (ix) Synovial membrane derived cells.

Another approach was the attempt to use natural occurring or synthetic biodegradable scaffolds which support three-dimensional growth of cartilage cells. The scaffolds may be impregnated with cells, which together with the scaffold form the graft. Alternatively, the scaffold may initially be devoid of impregnated cell, and endogenous cells from the patient are expected to migrate into the scaffold after its implantation.

Examples of such scaffolds are: (a) Fibrin polymers; (b) Collagen Type I; (c) Natural hyaluronic acid (HA) and chemically modified HA and (d) Synthetic biopolymers either biodegradable e.g. polylactic acid, polyglycolic acid or non-biodegradable (e.g. alginic acid). However, none of the above scaffolds can induce regeneration of hyaline-like cartilage. Fibrin adhesive polymers tend to induce dedifferentiation and thus do not permit production of functional tissue. Collagen Type I has no inherent chemotactic ability for chondrocytes, but stimulates proliferation of fibroblasts. Thus, instead of encouraging migration of chondrocytes, the tissue formed in this scaffold tends to be fibrous. Hyaluronic acid can stimulate chondrogenic differentiation, but does not stimulate chondrocytes proliferation. Alginic acid is a foreign sea weed derived carbohydrate and thus might induce an antigenic reaction, and furthermore it is not biodegradable. Polyglycolic and polylactic acid scaffolds do not support good hyaline cartilage regeneration due to acidic conditions formed during their degradation.

Damaged or missing hyaline cartilage is frequently repaired by transplantation of homografts. Homografts are immunologically privileged since the matrix acts as a barrier that permits only limited diffusion of low-molecular weight substances and contains an anti-angiogenesis factor to prevent invasion of host blood vessels and fibroblasts.

Various culturing systems have been developed for maintaining the viability and growth of tissues in culture. Generally, these are divided into static and perfusion bioreactors. Perfusion bioreactors are reactors which essentially keep constant, growth permissible conditions (such as nutrition, gas composition, temperature, pH, etc.) in which the growth fluid medium is constantly perfused in and out of the system. Typically, perfusion is carried out by utilizing a constant velocity flow of the medium.

SUMMARY OF THE INVENTION

By a first aspect, the present invention concerns a scaffold for use as growth supportive base for cells and tissue explants from three-dimensional tissue, comprising a naturally derived connective or skeletal tissue which has been treated for elimination of cellular and cytosolic elements, and which has been modified by cross-linking with an agent selected from the group consisting of: hyaluronic acid, proteoglycans, glycosaminoglycan, chondroitin sulfates, heparan sulfates, heparins and dextran sulfates.

By a second aspect, the present invention concerns a scaffold for use as growth supportive base for cells and tissue explants from three-dimensional tissue, comprising a naturally derived connective or skeletal tissue which has been treated for elimination of cellular and cytosolic elements, and which is formed of flakes having a size below $1000\mu$, which are attached to each other, the scaffold having a porosity of at least 85%, most preferably a porosity of 95%–98%.

By a third aspect the present invention concerns a scaffold for use as growth supportive base for cells and tissue explants from three-dimensional tissue, comprising an aggregate of at least 3, preferably 7–8 embryonal epiphyses, obtained from a third to midterm old fetuses (11 days old chick embryo, or 17–22 weeks human embryos). The aggregates are formed spontaneously, when several individual epiphyses are attached to each other, due to the presence of mesenchymal progenitor cells in the periphery of the epiphysis, cells which feature high expression of adhesive molecules such as integrins, cadherins and CAMs.

It has been found that such scaffolds according to the first, second and third aspects of the invention, have the properties of encouraging cells' adherence both to the matrix and to other cells as well, and enablement of propagation of cells. It was further found that the scaffolds of the invention supports chondrocyte proliferation at the expense of fibroblasts, resulting in a hyaline-like reparative repair tissue. Cross-linking with the agents specified above in connection with the first aspect gives the scaffold an additional mechanical strength and produces a substance which is less brittle with prolonged biodegradation time.

The term "scaffold" in the context of the first and second aspects of the present invention refers to the connective/skeletal tissue which has been treated for elimination of cellular and cytosolic elements. In accordance with the first aspect of the invention, the scaffold has been modified by cross-linking as described above. In accordance with the second aspect, the scaffold is composed of attached flakes having a size of less than $1000\mu$ and having porosity of at least 85%. This term also refers in accordance with the first and second aspect to such a construct containing additional agents such as adhesive molecules or growth factors.

The term "flakes" refers to particles or chips produced as a result of crushing the connective tissue, to particles of a size less than $1000\mu$.

In accordance with the third aspect of the invention the term "scaffold" concerns freshly aborted human epiphyses from around midterm ($18\pm4$ weeks), which are composed of mesenchymal progenitor stem cells and committed chondrocytes. At least 3 and preferably 7–8 epiphyses have been fused to form aggregates which could be formed spontaneously due to the adhesive properties of the mesenchymal cells. The aggregates were formed by growth in either static culture or in the system of the invention as will be described hereinbelow.

The term "three-dimensional tissue" (3D tissue) refers to any type of tissue which has an orderly three-dimensional structure, i.e., is not naturally present in the body in the form limited to a single layer of cells or lamina, but has a structure which is spatially ordered. Examples of three-dimensional tissue are: mesenchymal tissue, cartilage and bone tissue, liver tissue, kidney tissue, neuronal tissue, fibrous tissue, dermis tissue etc. Another three-dimensional tissue is the whole embryonal epiphyseal organ derived from embryos at a post limb-bud stage.

The naturally derived connective or skeletal tissue is, in general, a tissue that was derived from mesenchymal tissues that expresses, temporarily or continuously. fibroblast growth factor receptor 3 (FGFR3). Examples of such tissue are mainly members of the chondrogenic and the osteogenic anlagen, as well as the residual mesenchymal stem cell reservoirs found in tissues all along life, ready to carry wound healing, repair and regeneration tasks. Another example of connective or skeletal tissue is epiphyseal tissue, periosteal and perichondrial flaps that contain massive growth factors, and bone marrow.

In order to turn a tissue into a scaffold in accordance with the first and second aspects of the invention, the tissue should be treated for elimination of cellular and cytosolic elements such as: DNA, RNA, proteins, lipids, proteoglycans and in general most elements of the cells which are immunogenic, as well as treated for removal of calcification-mineralization centers. Methods for elimination of the above cellular and cytosolic elements are in general known in the art, preferably the elimination is achieved by alternating freezing and thawing cycles in distilled water serving as thoroughly washes, which eliminate lysed cells' contents, followed by incubation—evaporation in alcohol at 45–55° C. within an air blowing incubator.

The naturally derived connective or skeletal tissue treated as described above for elimination of cellular and cytosolic components, in connection with the first aspect of the invention, is preferably further treated for producing higher porosity, of the intact tissue, is by the production of pores in a controlled manner. The treatment may be mechanical, for example, by hammering the tissue on a scraper device, or by hammering a metal brush into the tissue (e.g. epiphyseal tissue).

Alternatively, the treatment for producing porosity may be a chemical extraction process carried out by exposing the tissue, for a controlled amount of time in a controlled environment, to chemical agents capable of partial degradation of the tissue. In addition or alternatively, the treatment for producing porosity may be carried out by exposing the tissue to enzymatic agents such as proteolytic enzymes, capable of partial degradation of the tissue. Example of such chemical agents which can produce pores in the tissue are guanidinium chloride. The pores should have preferably a size of $10$–$500\mu$, most preferably $20$–$100\mu$.

The agents either specified in above (i.e. hyaluronic acid, proteoglycans, glycosaminoglycan, chondroitin sulfates, heparan sulfates, heparin and dextran sulfates) or additional agents such as adhesive molecules or growth factor moieties may be linked to the residual scaffold either by sugar cross-linking, (for example using 1% of either ribose or xylose), by carbodiimide or by 1,1 carbonyl di-imidazole. Cross-linking with the above agents is generally carried out as known in the art of coupling in organic chemistry.

In accordance with the second aspect of the invention, the porosity is an inherent property of the scaffold of the invention, as the scaffold is made of flakes which have a size of less than about $1000\mu$, attached to each other, so that the overall porosity of the scaffold is above 85%, preferably above 90%, most preferably above 98%.

Such high porosity is obtained, after elimination of cytosolic elements, as described above, by crushing the connective skeletal tissue which has been treated for elimination of cellular and cytosolic elements, to small particles, preferably having a size below $1000\mu$ and then loosely attaching these small flakes to each other. One manner for such attachment, is by suspending the small flakes in alcohol, and then evaporating the alcohol in a vessel with a very large surface, resulting in a residue of material having a "crust-like" characteristic, with a very high porosity.

Preferably, the scaffold of the invention is composed of several, essentially single-flake layers of "crust-like material", arranged one on top of the other, most preferably a construct of at least 5 layers. Preferably, the layers are fused to each other at their edges, by heat-thermo treatings, for example by application of laser irradiation.

The fusions of the "crust-like" material may be improved by the addition of small amounts, of 10–40% albumin solution, these layers are added in the periphery of each layer.

By another aspect, the present invention concerns a method for the production of a scaffold for use as a growth supporting base for cells and tissue explants obtained from three-dimensional tissue, the method comprising:

(i) providing naturally derived connective or skeletal tissue;

(ii) eliminating cellular and cytosolic elements from said connective tissue;

(iii) crushing the connective tissue obtained in (ii) to produce flakes having a size of less than 1000μ;

(iv) suspending the flakes in alcohol;

(v) evaporating the alcohol in a vessel having a large surface face, thereby producing a scaffold which has essentially no cellular and cytosolic elements, and has a porosity of at least 85%, preferably 90%, most preferably 98%.

In accordance with the present invention, it is preferable that the scaffold also contains adhesive molecules in order to enhance cell adherence to the scaffold. Example of suitable adhesive molecules are the integrins and additional extra cellular constituents known to interact, agents such as, laminin, fibronectin, hyaluronic acid, polylysine, lysozyme and collagen. The formation of collagen, for example, may be enhanced by additions of ascorbic acid and its stable derivative such as ascorbic-2-phosphate. Said adhesive can be used in accordance with all three aspects of the invention.

In accordance with the present invention, it is also preferable that the scaffold would contain endogenously or exogenously added growth factors, in order to enhance the rate of growth of the cells filling the three-dimensional space of the scaffold. Examples of suitable exogenously added growth factors are: fibroblast growth factors (FGF's), TGF's, BMP's, IGF's. The growth factor chosen should depend on the type of tissue used. It should be noted that scaffolds of natural tissues, devoid of cells and cytosolic elements may still contain endogenous growth factors, bound to extracellular matrix elements so that at times the endogenous growth factors present in the matrix are advantageous ingredients.

By one option, it is possible to formulate a prosthesis from the scaffold alone in accordance with the first and second aspects of the invention, i.e. of a scaffold devoid of cells. In such a case, the scaffold is formulated to a desired shape and is inserted into the desired location in the body of the individual, for example, a location wherein it is desired to achieve invasion of endogenous mesenchymal cells such as in the knee joint.

The prosthesis is maleable and can be shaped as either a flat sheet of several millimeters in thickness or any other three-dimensional shape adapted to the shape of the lesion. As explained above in connection with the second aspect of the invention, the "crust-like" scaffold having a porosity of at least 85%, can be formed by stacking several single-flake layers on top of the other, preferably using at least 5 such layers. Most preferably the edges of the layers may be fused to one another to provide mechanical support, for example, by fusing them using adhesives with or without laser irradiation creating heat (60–70° C.).

Alternatively, the prosthesis, can, a priori, prior to implantation contain embedded (impregnated) cells, for example cells grown originally as monolayers or multi-layers on filters (Millicell cell culture [PICMORG50] inserts for use in organotypic cultures, 30 mm, low height, Millipore Corp. Bedford, Mass, USA), and placed 5–10 units in the device described further below, or tissue explants to allow their fast anchorage and integration into bone and cartilages.

The cells impregnating the prosthesis should preferably be from an autogeneic source, but can also be of an allogeneic source, as cartilage has a sort of an immunoprivilage.

The scaffold of the invention according to both the first and second aspects of the invention (after treatment for elimination of the endogenous cellular elements) can be impregnated with exogenous cells, not only for direct implantation in the body but also for prolonged in vitro growth and differentiation of various three-dimensional tissues kinds such as skin, neuronal, bony, cartilaginous, liver, pancreatic beta cell and almost of any organ or tissue in a bioreactor, while adjusting the proper medium, cocktail of growth factors and adhesive molecules.

By another aspect the present invention concerns a system for maintaining viable three-dimensional tissue.

Static cultures in regular incubators can support cell growth in monolayers, multilayers or at most few microns 50–100 micron of 3D explants. For larger 3D explants only special bioreactor devices can support growth by perfusing nutrients, gases and remove wastes.

In accordance with this second aspect, it was surprisingly found that for long-term maintenance of viable three-dimensional tissue, there is need to apply rhythmic pulses of pressure (hydrostatic, mechanical or shear force) in order to obtain optimal growth. For example for growing of an articular cartilage tissue there is an advantage in maintaining the tissue under repetitious cycles of loads and unloads of pressure in a rhythmic manner, simulating the natural growth conditions in the joint. The cellular mechanoreceptors seem to play a key role in this respect of cell growth.

The variables that can be manipulated in the system of the invention include stream flow velocity, amount (in atmospheres) of hydrostatic and/or mechanic pressure, rhythmic action periods (frequency of applications of pressure) and pausal intervals (pulses), as well as change stream direction of the medium. By this second aspect, the present invention concerns a system for the maintenance of viable tissue comprising:

(ix) a chamber for holding the tissue, the chamber's atmosphere being kept at a relatively constant gas composition, said gas composition being suitable for maintenance of viable biological tissues;

(ii) a reservoir for holding tissue culture medium, said reservoir being in flow communication with the chamber;

(iii) a pump for circulating the medium between the chamber and the reservoir in a controlled manner; and (iv) a pressure generator for producing rhythmic pulses of pressure on the tissue present in the chamber.

The system of the invention is suitable for any type of cells or tissues, but is especially suitable for the growth of a three-dimensional tissue, according to the definition above.

Basically, the system comprises a chamber for holding the tissue, the chamber's atmosphere being kept at relatively constant gas and temperature composition which are suitable for maintenance of viable biological tissue, for example 5% to 10% $CO_2$ in air at physiological temperature. This is usually achieved by placing the chamber within a larger $CO_2$ incubator, capable of maintaining such an atmosphere, and ensuring that the atmosphere of the incubator in communication (as regards temperature and gas composition) with that of the chamber.

The system farther comprises a reservoir for holding tissue culture medium which is in flow communication with the chamber. Preferably, the size of the reservoir is about 30 to 100 times larger than that of the chamber for holding the tissue and is typically the size of 400–1000 ml. The medium in the reservoir of course contains the nutrients and various agents such as growth factors, etc. required for maintaining viability and growth of the tissue.

The system comprises a pump which circulates the growth medium between the chamber and the reservoir in a controlled manner. The pump may be a constant pump or a peristaltic pump utilizing either computerized or electrical/electronical manipulated regimes, as will be explained hereinbelow. Typically, the velocity of medium flow is in the range of 300–600 ml/min.

The pressure generator may produce mechanical or hydrostatic pressure on the tissue and may be, for example, a compressor (piston) present in the chamber, which can periodically apply pressure on the tissue present in the chamber when streaming in one direction and the pressure is released when streaming in the other direction. The compressor should be under control of a control mechanism capable of controlling the timing (frequency, pausal, etc.) and the level of compression, such as a clock or a computer mechanism.

The control mechanism would trigger the compressor, to compress the chamber thus applying rhythmic pressure on the liquid present therein, and consequently applying pressure on the tissue. In the case of a compressor, the pump's activity may be constant so that the medium circulates between the chamber and the reservoir at a constant rate in order to improve gas exchange and nutrient availability to the tissue.

By another alternative, the pump that circulates the medium between the chamber and the reservoir is itself the pressure generator capable of producing rhythmic pulses of hydrostatic pressure on the tissue. In that case the pressure generator is the pump itself and no additional elements (such as a compressor) are required to produce the rhythmic pulses of pressure. The pump which is a peristaltic may have a built-in means for triggering rhythmic pulses. Alternatively, the pump may be connected to a control mechanism which triggers the duration, delays and frequencies of the pump such as a clock or a computer mechanism.

By alternating activities of such a pump, the medium can circulate in pulses between the medium reservoir and the chamber, thus creating rhythmic pressure pulses on the tissue. Preferably the direction of the medium flow should be changed (for example clock-wise and then counter-clockwise) as changing the flow direction simulates best the joint's conditions of loading and unloading. Typically change of direction should be every 1 to 3 min.

The rhythmic pulses should have a frequency of 5–300 per min., preferably 10–200 per min., most preferably 60 to 120 per min.

The hydrostatic pressure should be between 0.5 and 30 atm., preferably 1 to 10 atm, most preferably 2 to 3 atm.

The present invention concerns a method for maintaining viable tissues, cells or explants from three-dimensional tissue, comprising placing these tissues in the chamber of the above system with any of the above parameters of pressure, frequency and change of flow direction. Examples of tissue are as defined above in connection with the scaffold.

The present invention further provides a method for maintaining viable cells or tissue explants from three-dimensional tissue comprising growing a prosthesis composed of the scaffold of the invention (in accordance with both aspects) impregnated with cells in the system of the invention with conditions specified above (i.e. the parameters specified above). A preferable example is a method for growing fresh cartilaginous tissues such as embryonal epiphyseal tissue, turning to an allogeneic implant upon in vivo transplantation.

DETAILED DESCRIPTION OF THE PERFUSION DEVICE OF THE INVENTION

Figure 1:
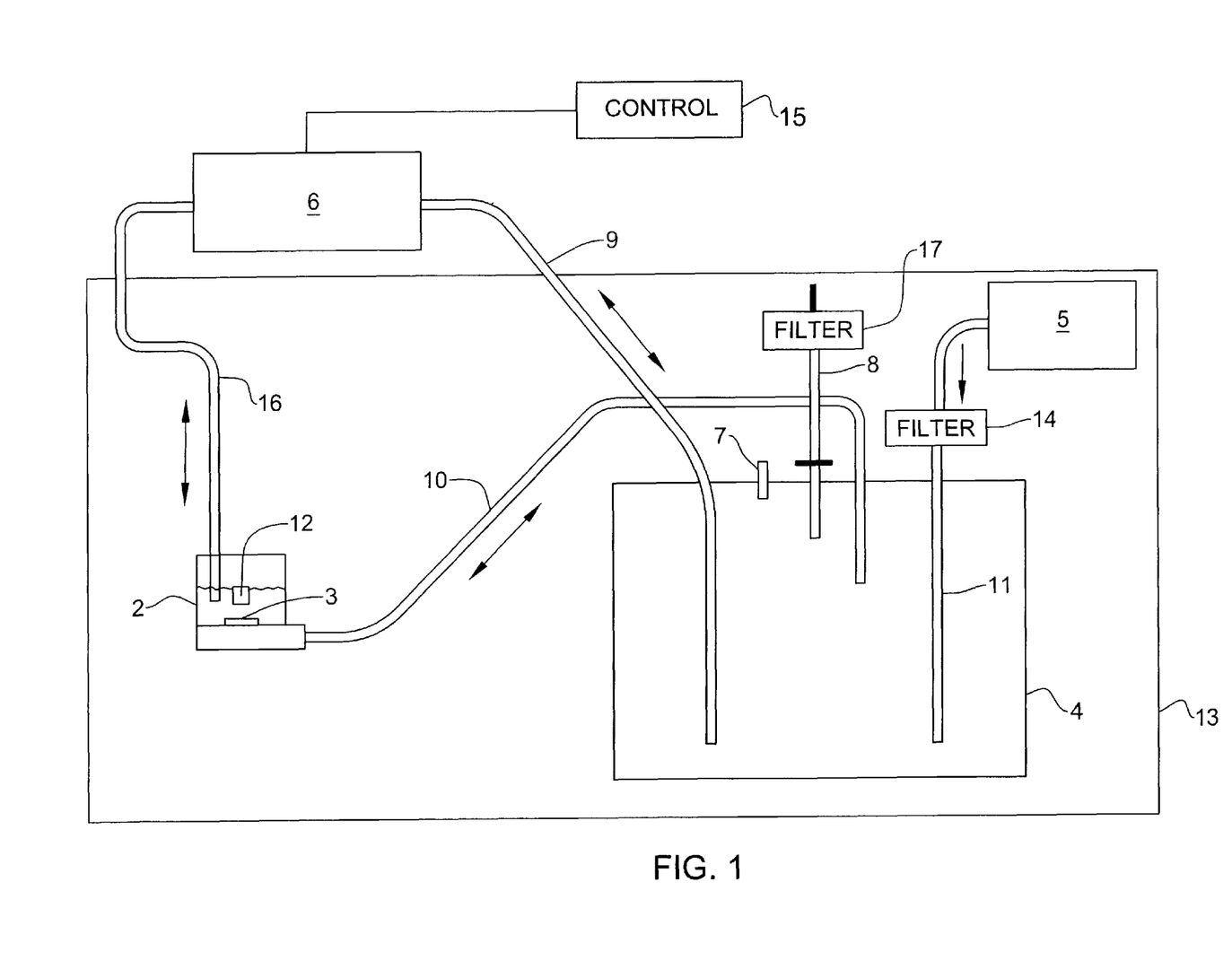
FIG. 1 shows a schematic representation of the system of the invention for maintaining viable three-dimensional tissue.

Reference is now made to FIG. 1 which shows an embodiment of the system of the invention 1. The system is composed generally of a chamber 2 which holds within scaffold 3 of the invention impregnated with exogenous cells (e.g. autologous chondrocytes or even intact embryonal epiphyses serving as future allogeneic cell implant), or for example scaffold made of embryonal epiphysis tissue (devoid of the endogenous cells, thus impregnated with exogenous ones). The system further comprises a medium-containing reservoir 4 which is filled with a media capable of supporting and maintaining viable cells. Medium flows from chamber 4 through out flow tube 9 into pump 6 and then through tube 16 into chamber 2. The medium then returns to the reservoir through connecting chamber outflow tube 10. The circulation of the medium is mediated through pump 6. In the present example, the pump is the element creating rhythmic pressure by its rhythmic activities and is a peristaltic pump. By other examples the pump may work continuously and rhythmic pressure may be created by other independent means such as a compressor.

The chamber and the reservoir are enclosed in $CO_2$ equilibrium incubator 13, which maintains constant gas and temperature. In reservoir 4, there is a small aquarium pump 5 and filter 14 for circulating the medium in the reservoir, filtering out particles and contaminants. The reservoir also includes needle valve 8 to equilibrate and release pressure, as well as gases outlet 11. Chamber 2 includes a mechanical plunger 12.

The system also comprises control mechanism 15 which can be a computer and in this case is an electrical-electronic controlling device. The computer controls the timing, duration, pausing of the activity of pump 6 as well as the direction of the flow in the system. Thus, by giving the computer correct parameters, it is possible to activate pump 6 rhythmically so that it can work and pause alternatively resulting in streaming which will cause hydrostatic pressure on the cells present in scaffold 3 in chamber 2. Furthermore, by this control the pump may change the direction of the flow of medium. It may initially flow in the direction of 4→9-6→16-2→10→4, and then the direction may be reversed so that it flows in the reverse direction.

The volume of reservoir chamber 4 is preferably about 50 times that of chamber 2.

The chamber 2 and the medium reservoir 4 are enclosed in an incubator 13 at 37° C. and a pH of 7.25±0.05.

EXAMPLE 1
Tissue Maintenance in the System of the Invention

Maintenance of whole embryonal epiphyses both as a separated organ, or as several epiphyses fused together occurred in the system of the invention.

Experiments were conducted both in vitro and in vivo in an avian model, while human, embryonal epiphyses of aborted fetuses were experimental in vitro only. Whole epiphyses used further as implants transplanted by squeezing them (press fit) into articular defects (animal experimentation).

Maintenance was achieved by keeping the epiphyses in the device shown in FIG. 1 for 10–20 days. Vitality was assessed by histology, $^{35}$S-sulfate incorporation into isolated glycosaminoglycans and by XTT test (as explained below in Example 6). The results are shown in FIGS. 2(a) and 2(b).

Figure 2A:
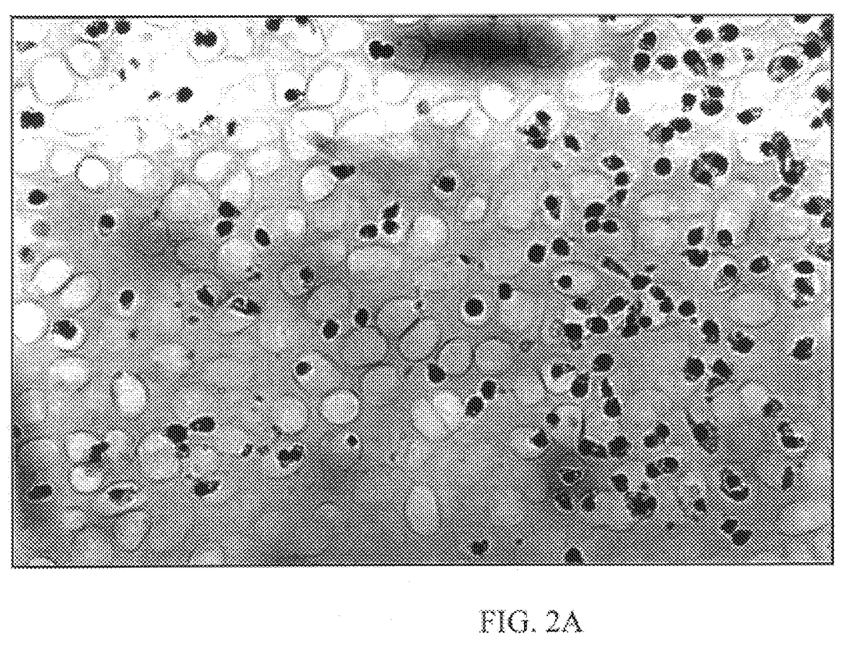
FIG. 2(a) shows a histological section from whole embryonal epiphyses maintained under static growth conditions in a growth medium.
Figure 2B:
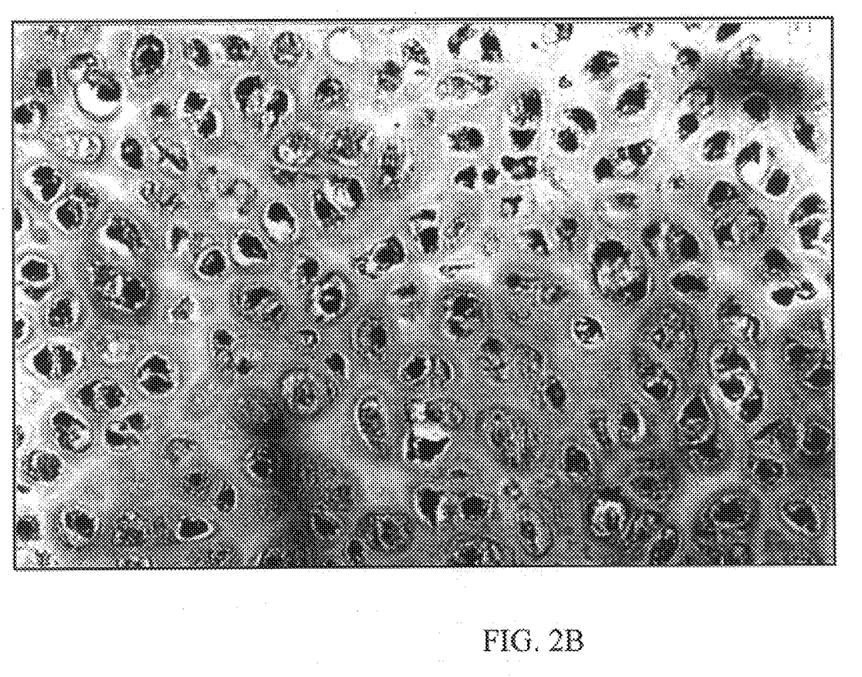
FIG. 2(b) shows histological sections from whole embryonal epiphyses maintained in the perfusion system of the invention under conditions of rhythmic pressure.

FIG. 2(a) shows tissue prepared as above kept in an incubator under static conditions (i.e. with no effects of rhythmic pressure). As can be seen the tissue is necrotic as evident by lysis of cells and spilling out of the nuclei to the medium. Against this FIG. 2(b) shows the same tissue kept in the perfusion system of the invention. The tissue remained viable with intact cells. These results show that the system of the invention is advantageous for maintaining viable tissue for prolonged periods of time.

EXAMPLE 2
Inducing Repair in Articular Defects.

Defects were created in vital-fresh articular cartilage of an adult bone epiphyseal heads which were placed in a system as described schematically in FIG. 1. The epiphyseal heads were grown and maintained in the system for 7–14 days to induce regeneration and repair in the tissue either by transplanting cells in adhesives or whole epiphyses. The results (not shown) indicate that cell and tissue integration and propagation within the defects took place, signifying that the system of the invention enables the initial repairment stages of defects in tissue in vitro and development of a new reparative tissue.

EXAMPLE 3
Scaffold Preparations From Embryonal Epiphyses, Soft and Calcified Connective Tissue Shunks Epiphyses from aborted human fetuses (15–25 wks) were collected, cleaned from soft tissues and underwent 5 cycles of freezing and thawing in distilled water and washed thoroughly by phosphate buffered saline after each cycle, in order to get rid of cells and cytosolic residues. These tissue residues containing basically matrices enriched by growth factors, were further bored to increase porosity, making holes and channels by a specially designed metal brush.

Cortical and cancellous bone, articular, meniscal and tracheal cartilages all underwent basically the same chemical-enzymatic and mechanical procedure for their adjustment as a scaffold. The scaffolds were used for cell and tissue explant adherence and growth, in the process of in vitro reconstruction of composite engineered cartilaginous implants to induce regeneration and repair in damaged articular cartilages.

1. The tissue samples were cleaned of soft tissue residues and underwent three cycles of freezing and thawing using liquid nitrogen for freezing and double distilled water for thawing, followed by three washes in phosphate buffered saline (PBS) at pH 7.4, getting rid of the cytoplasmic content of the lysing cells.
2. The tissue samples were further extracted by constant stirring in 4 M guanidinium chloride for 48 hours in the cold room. After thoroughly washes in dH$_2$O, removal of all chlorides was assessed using AgNO$_3$.
3. Calcified tissue further underwent a decalcification step by either EDTA, acids or special reagents, followed by thoroughly washes with distilled water and PBS.
4. For removing lipids the samples were extracted by constant stirring with chloroform:methanol (1:1 v/v) in the cold room, until no more yellowish substances were extractable. To remove the organic solvents the samples were washed with PBS for overnight under constant stirring in the cold.
5. A short collagenase digestion (37.5 units/ml) was performed for one hour in PBS at 37° C. The digestion was terminated and followed by rinsing twice in saline (0.9% NaCl).
6. The collagenase treatment was followed by a short papain further (proteolytic) digestion (25 μl Sigma concentrate/ml papain buffer (pH 5.4) containing cysteine (1 mg/ml)).
7. The samples were rinsed 5 times in saline enriched by antibiotics.
8. Production of pores was performed by hammering the tissue over a scraper and rinsing with PBS.
9. The tissue samples were kept sterile and frozen until it was collected for in vitro reconstruction with cells or tissue explants, designed for implantation.

Variation of this procedure is dependent on the exact consistency of the original tissue used.

EXAMPLE 4
Sugar Cross-Linking of Matrix Agents Added to Natural Tissue to be Used as Scaffold One percent solutions of hyaluronic acid, cartilage proteoglycan-aggrecan, various glycosaminoglycans, (chondroitin sulfates. keratan sulfates, heparan sulfates (syndican and perlican)), dextran sulfate (synthetic), egg lysozyme, polylysine (synthetic), arteparon ect., were mixed with either 1% ribose or 1% xylose in the cold in suspension with the treated tissue scaffold, for 3 days in the cold room. Then the tissue samples were washed thoroughly in PBS.

EXAMPLE 5
Implant Scaffolds Impregnated With Cells

Cells from human arthroscopic biopsies, perichondrium and periosteum were cultured to a cell density of 10$^7$ cells/cm$^2$. Scaffold enriched with matrix constituents were formed from one of the following: (1) demineralized bone matrix; (2) modified cross-linked small intestine submucosa and (3) acellular matrices of embryonal epiphyses, in accordance with the third aspect of the invention.

Demineralized cortical and spongious bone were treated mechanically to produce porosity by hammering the tissue over a scrapper device.

Pig small intestine submucosa (SIS) deficient of its endothelial layer was modified by guanidinium chloride extraction, and sugar cross-linking as explained above. Hyaluronic acid and chemically altered hyaluronic acid molecules. The above human arthroscopic derived dedifferentiated cultures were used as cell source for impregnating the scaffolds.

Human embryonal epiphyses were treated to eliminate (devitalize) the cells, thus leaving the matrices and their absorbed molecules (e.g. growth factors) intact. Increased porosity was obtained by booring a metal brush into the tissue.

Figure 3A:
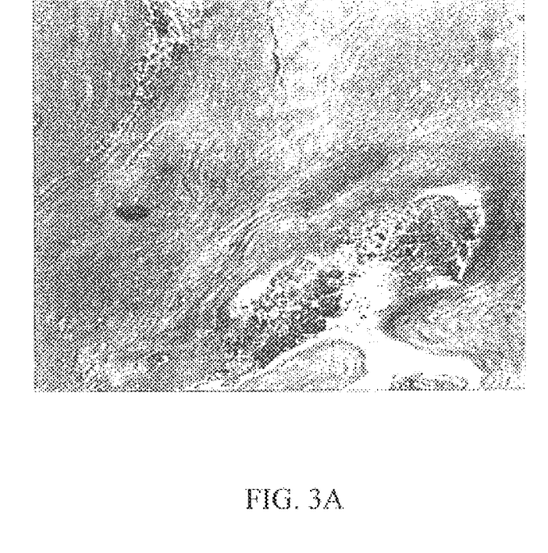
FIGS. 3(a)–(d) shows histological cross-sections of scaffolds of the invention composed of demineralized cortical and spongious bovine bone modified by cross-linking, which is impregnated with human chondrocytes.
Figure 3B:
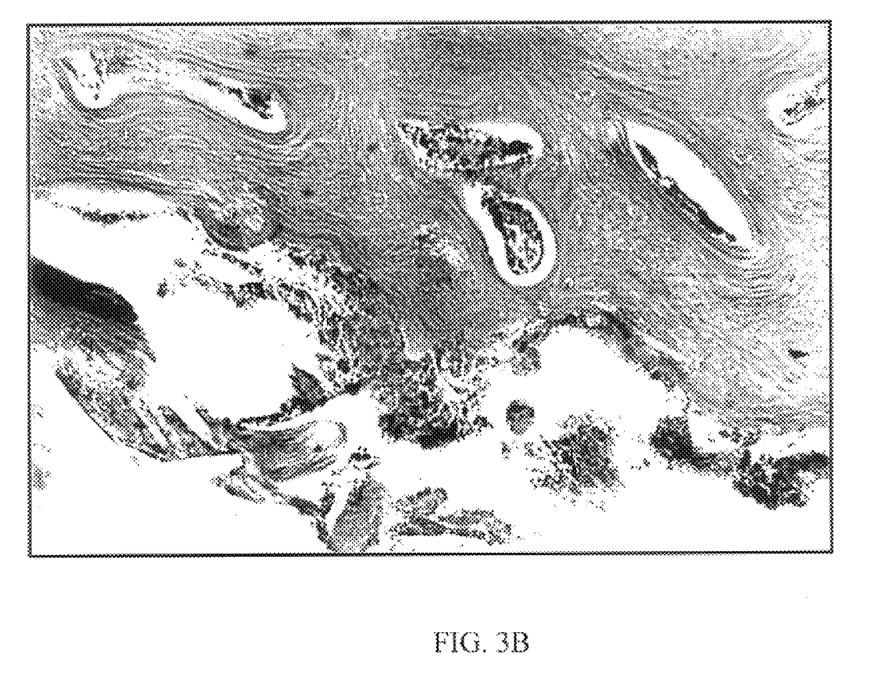
Figure 3C:
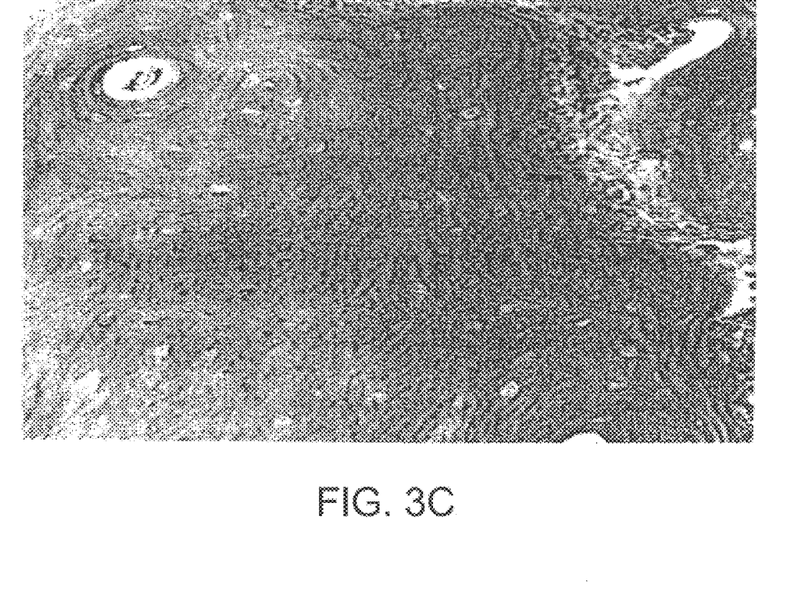
Figure 3D:
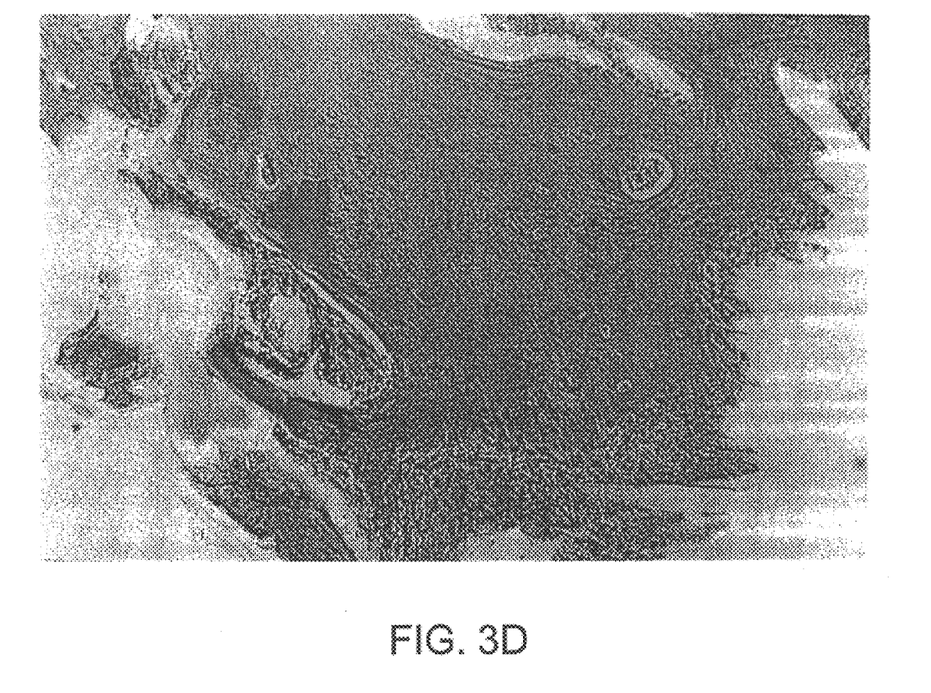
Figure 4A:
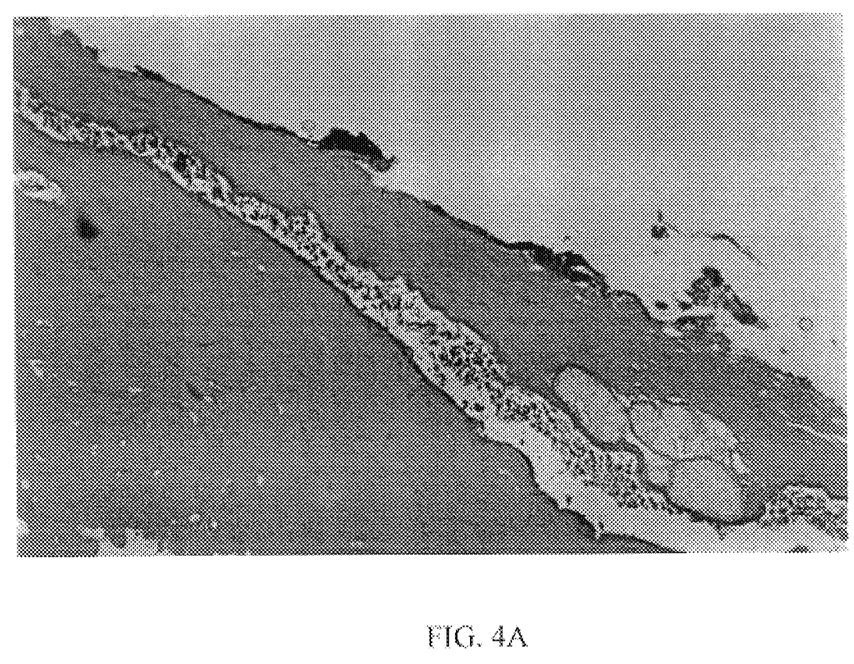
FIGS. 4(a)–(b) shows histological cross-sections of scaffolds of the invention composed of pig small intestine submucosa (SIS) modified by cross-linking, impregnated with human chondrocytes.
Figure 4B:
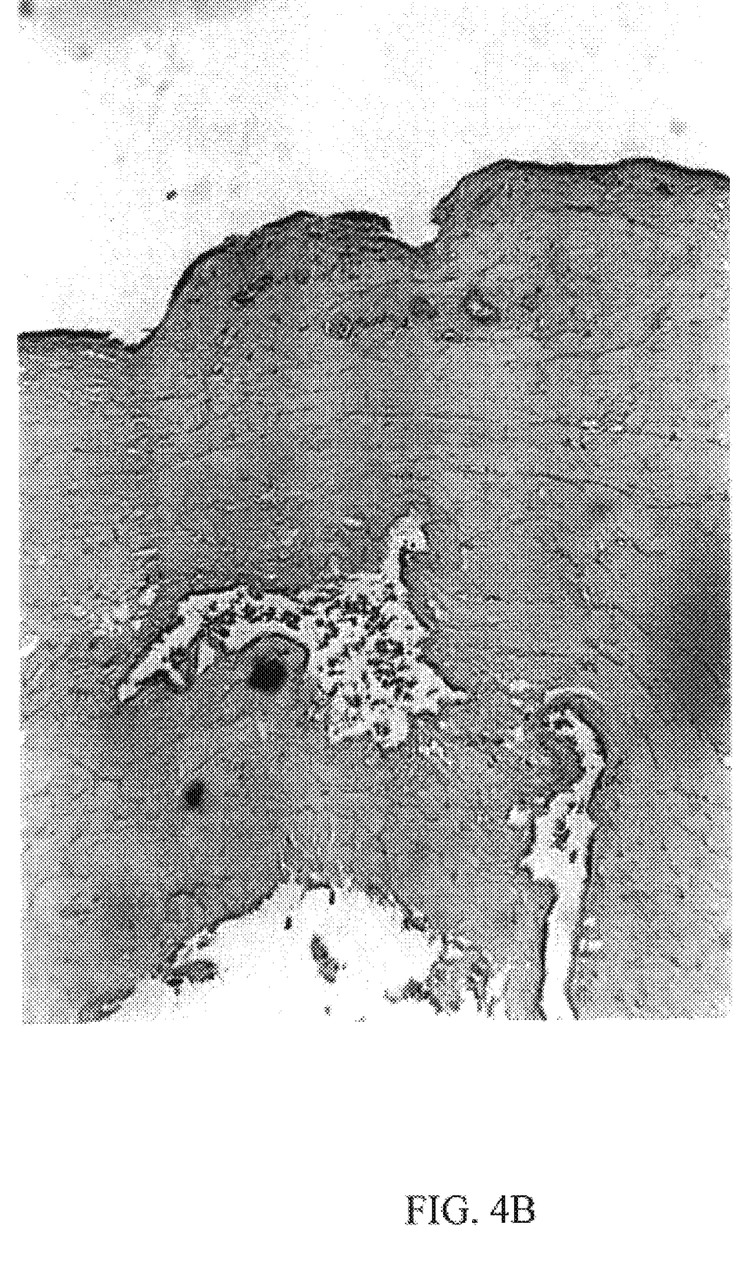

The results are shown in FIGS. 3(a)–3(b) which show several different histological preparation of demineralized cortical and spongious bovine bones impregnated in cells and in FIGS. 4(a) and 4(b) which show a pig small intestine submucosa (SIS) devoid of its endothelial layers modified by guanidinium chloride extraction and cross-linked as above.

As can be seen, the two types of the above scaffolds of the invention supported maintenance of viable cells, show normal morphology.

EXAMPLE 6
Embryonal Epiphyses as Implants to Repair Articular Cartilage Defects With and Without Embedding in a Scaffold.

Fresh embryonal epiphyses were isolated and cleaned of soft tissues of long bones tibias and femurs of aborted fetuses at mid gestation (18 weeks±4) (the younger gestation age the better). The isolated and cleaned epiphyses can be maintained vital for weeks, up to the need for implantation, under a constant perfusion in the system of the invention. The separated epiphyses hold together (e.g. in a Nitex-20 mesh) tend under these cultured conditions to associate (fuse together) into one tissue piece forming aggregates in accordance with the third aspect of the invention. The vitality of the newly formed tissue compared to epiphyses maintained under regular static culture conditions was assessed by:

(i) Histology, histochemistry and immunohistochemical staining procedures, (ii) Incorporation of $^{35}$S-carrier free sulfate into isolated glycosaminoglycan macromolecules, and (iii) By XTT reagent measuring cell vitality in a standard tissue ring specimens by reduction of tetrazolium salts by the cell's mitochondrial hydrogenases, yielding a soluble colored molecule—a formazan dye, measured at 450 nm with an ELISA plate reader. The optical density is proportional to the number of living cells and their metabolic status.

These biological in vitro reconstructed (engineered) tissues have clear advantages as implants as follows:

(i) The engineered in vitro reconstructed cartilaginous implants are readily malleable to fit the exact shape and size of the articular defects.

Figure 5:
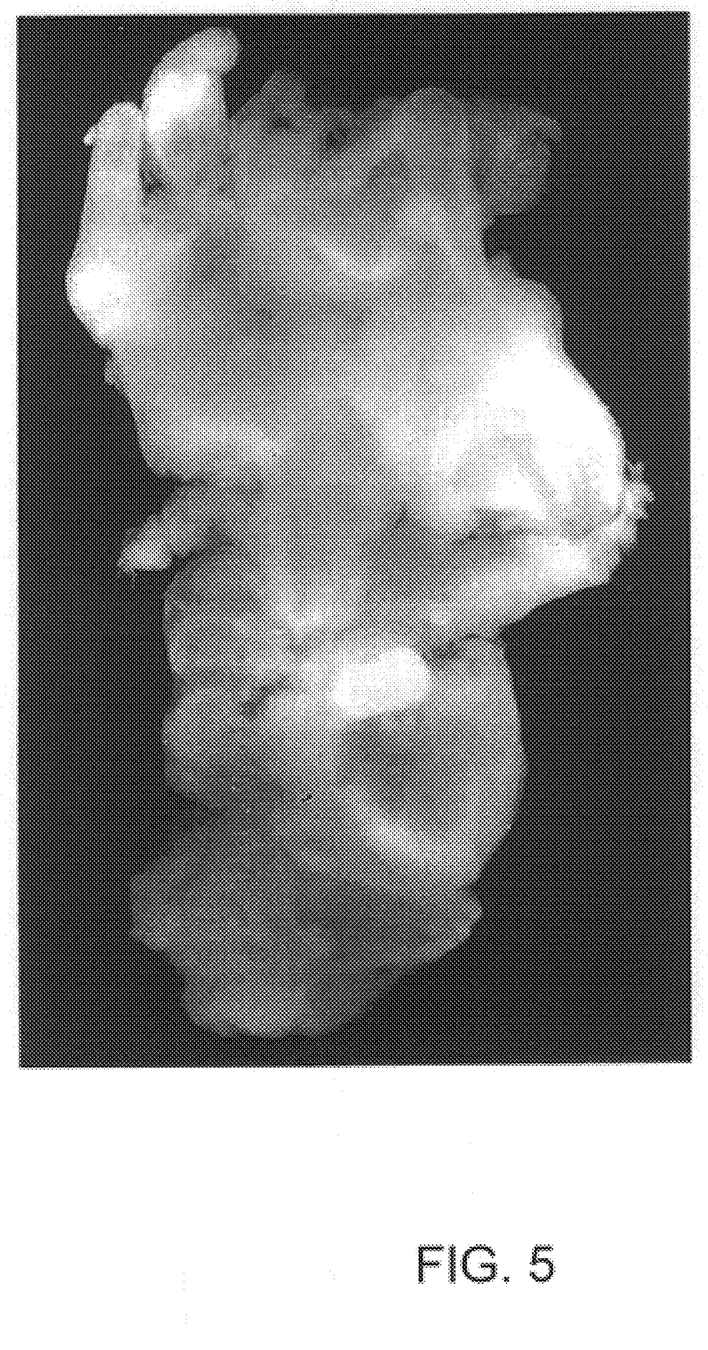
FIG. 5 shows embryonal epiphyseal tissue resulting from spontaneous fusion.
Figure 6:
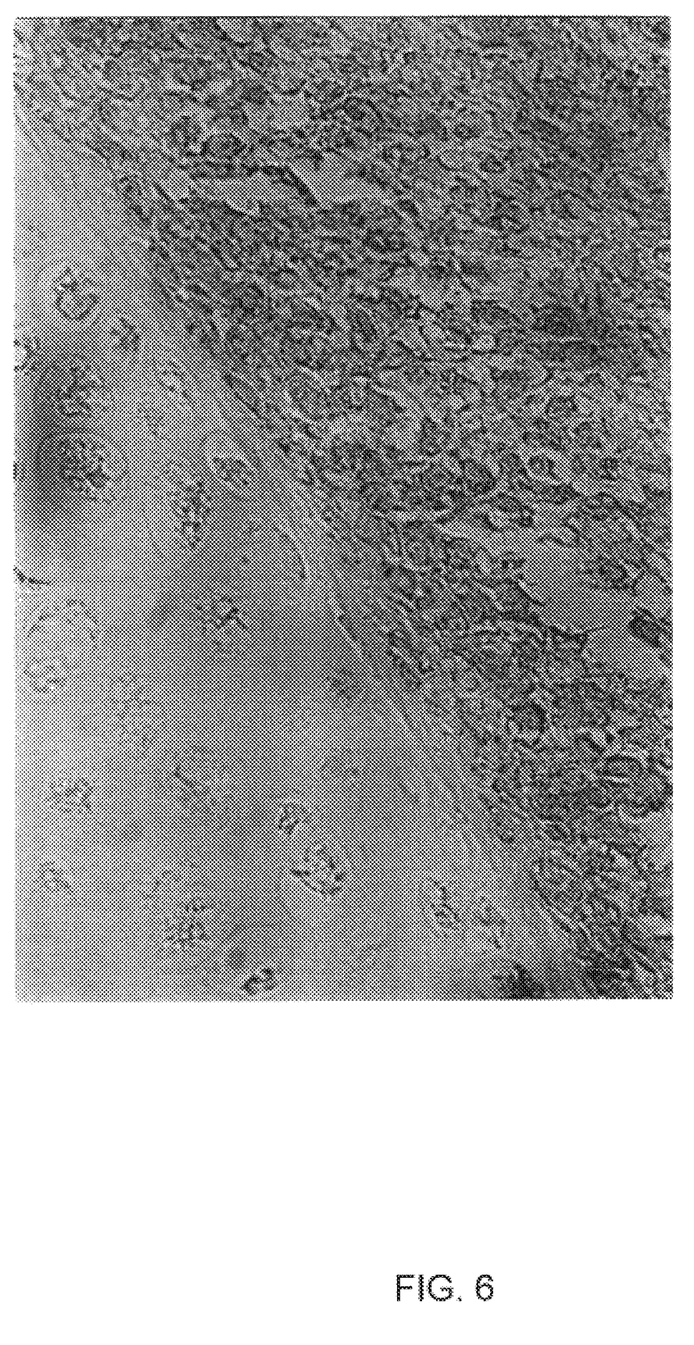
FIG. 6 shows a histological section of the tissue of FIG. 5.

(ii) They are readily squeezed in (press fitted) and strongly held (anchored) into the lesion sites, integrating rapidly with the neighboring cartilage and bone tissues FIG. 5 shows epiphyseal tissue which has been spontaneously fused, maintained and in the system of the invention demonstrates that the system of the invention can maintain relatively large pieces of tissue in viable state for extended periods of time. FIG. 6 shows a histological cross-section of the tissue of FIG. 5. As can be seen, the system of the invention supports the viability of a large range of different cells at a wide range of differentiated stages as evident from the fact that various stages of differentiation were maintained in a viable state.

EXAMPLE 7
Method of Preparation of "crust-like", High Porosity Scaffold

Human embryonal fresh epiphyses were collected from aborted healthy fetuses (17–22 weeks) or from any other animal model. The sterile collected epiphyses were cleaned off residual soft tissues in calcium-magnesium free Hank's solution. The cleaned epiphyses were put aseptically in 70% ethanol and underwent a massive grinding an a polytron (Kinematica GMBH, Luzern, Schweiz) for 10 minutes in ice.

The obtained suspension with the epiphyseal flakes (crumbs/chips) was placed on top of a sieve (Ari J. Levy Ltd. Bne Brak, Israel ASTM # 18; 1000 micrones) and the epiphyseal flakes that came through were collected by contrifugation as a pellet. The cleaned and sieved epiphyses flakes resuspended in sterile distilled water underwent further processing by a series of freezing and thawing cycles (X5) in doubled distilled water in order to lyse the cells (chondrocytes), leaving intact extracellular matrix—the milieu is believed to contain a rich resservoir of hormones, growth factors signaling molecules etc.

At the termination of cell lysing procedure the flakes underwent repetitious washes in sterile water, to get rid of the residual cytosolic substances released from the lysing cells. The treated flakes were again centrifuged and washed thoroughly in ethanol, forming an ethanol suspension of flakes. The flakes precipitated out from the ethanol solution in a ventilated incubator at 45°–55° C. forming a stable crust. The crust was collected mechanically by scraping, creating plates (tile like particles) of various size. The crust was kept dry till use in the cold, 4° C.

EXAMPLE 8
Addition of Cells to "crust-like" High Porosity Scaffold

Pieces of epiphyseal crusts (flakes) were placed in a regular tissue culture plate and pellets of cells were added onto the crust, then, a limited amounts of medium was added. The crust was imbibed (hydrated) with the culture medium forming a viscous colloid type formate, that still enables after various growth periods, to be picked up (collected) by forceps and shook in medium to get off non attached cells. These cultures were held as static cultures for 24–48 hrs to allow the cells to adhere and then the 3D formate was formed by stacking at least 5 layers and placed in the device (JSD). There these constructs grew for days to a month, and compared to static cultures where the medium was replaced twice a week. At termination of the incubations, the crust of the two kinds of culture were placed in new plates and tested with the XTT reagent, measuring mithochondrial hydrogeneses for vitality assay in comparison to control pieces of epiphyseal crust without seeded cells.

Figure 7:
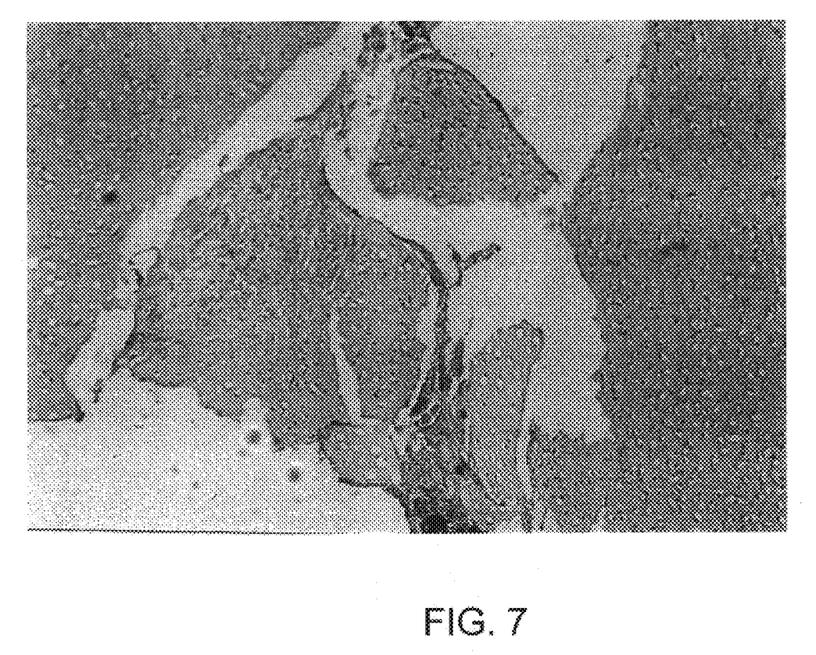
FIG. 7 shows a photomicrograph of human embryonal epiphyses flakes, under 1 mm. In diameter. Control without added cells (H&E X 100)
Figure 8A:
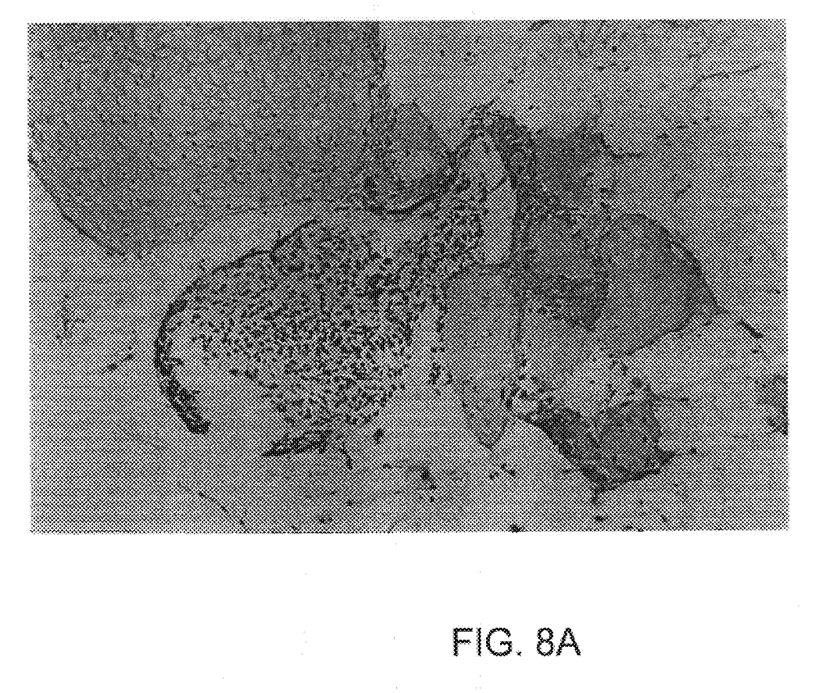
FIG. 8a shows a microphotograph of human embryonal epiphyseal flakes seeded with human embryonal chondrocytes, grown for a month in regular static (H&E;X100).
Figure 8B:
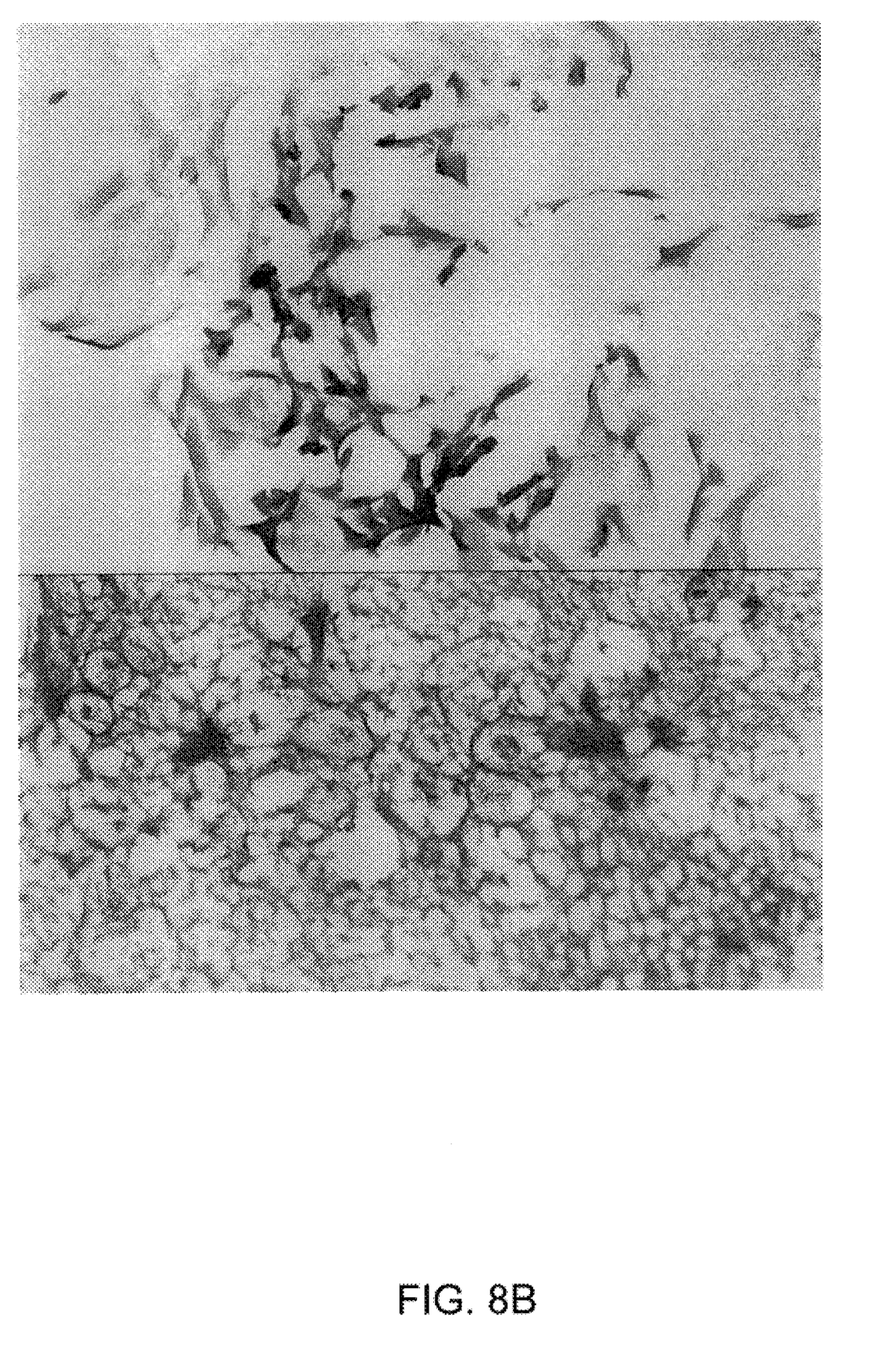
FIG. 8b shows enlargement of the colony of added cells shown in FIG. 8a (H&EX 400).

With increased time in culture more and more intense staining occurred under standard testing conditions (as shown in FIGS. 7 and 8). Reconfirmation of the biochemical-cellular findings with the XTT reagent was obtained by histological and histochemical examinations of sections, prepared from the very same two pieces of crusts. The results prove that the new scaffold serves as a friendly substance for cells in culture, with a clear advantage to the JSD growth conditions.

An alternative method for seeding onto cells, the crust flakes were produced from the epiphyses spinning in small Spinner bottles containing high concentrations of cells in the suspension. Cells from the suspension were proven to attach the flakes within 24 hours. Longer periods of 48 and 72 hours increased the concentrations of attached cells, again measured by the XTT reagent and histological-histochemical examinations.

The creation of multilayer of crust flakes formed a 3 dimensional tissue-like construct that survive in a static culture plates for a few days only, while its maintenance in the system of the invention, a kind of bioreactor, where the crust flakes were added onto rings with metal net-like bottoms, placed in a cylinder type container, one above the other, while the fluid was flowing through a rythmic pace and pressure, resembling the physiological candidates in the circulation of the body.

EXAMPLE 9

Detailed Procedure for the Production of Epiphyseal Flakes
1. Epiphyses were crushed by a polytron and flaked were formed.
2. Flakes passing through sieves having a size of under 1000μ were collected, washed in alcohol and resuspended in sterile distilled water.
3. The resulting flakes (pellet) underwent 5 additional cycles of freezing and thawing in distilled water to remove cellular-cytosolic residues.
4. The flakes were resuspended in alcohol and placed, as a thin layer in a vessel having a large surface face and was evaporated in an oven at 45–55° C., with constant ventilation for getting rid of the ethanol.
5. The result was a "crust-like" scaffold material having a high porosity, of about 95–98%. A solution of 10–40% albumin was used to adhere the layers of the crust made of the epiphyseal flakes to each other.

EXAMPLE 10

Preparation of Scaffold Tissue for Elimination of Cellular and Cytosolic Elements Cortical and cancellous bone, articular, meniscal and tracheal cartilages all underwent basically the same chemical-enzymatic and mechanical procedure for their adjustment as a scaffold. The scaffolds were used for cell and tissue explant adherence and growth, in the process of in vitro reconstruction of composite engineered cartilaginous implants to induce regeneration and repair in damaged articular cartilages.
1. The tissue samples were cleaned of soft tissue residues and underwent three cycles of freezing and thawing using liquid nitrogen for freezing and double distilled water for thawing, followed by three washes in phosphate buffered saline (PBS) at pH 7.4, for getting rid of the cytoplasmic content of the lysing cells.
2. The tissue samples were further extracted by constant stirring in 4 M guanidinium chloride for 48 hours in the cold room. After thoroughly washes in $dH_2O$, removal of all chlorides was assessed by the lack of whitish precipitate upon using $AgNO_3$ solution,
3. Calcified tissue further underwent a decalcification step by either EDTA, acids or special reagents, followed by thoroughly washes with distilled water and PBS.
4. For removing lipids the samples were extracted by constant stirring with chloroform:methanol (1:1 v/v) in the cold room, until no more yellowish substances were extractable. To remove the organic solvents the samples were washed with PBS for overnight under constant stirring in the cold.
5. A short collagenase digestion (37.5 units/ml) was performed for one hour in PBS at 37° C. The digestion was terminated and followed by rinsing twice in saline (0.9% NaCl).
6. The collagenase treatment was followed by a short papain further (proteolytic) digestion (25 μl Sigma concentrate/ml papain buffer (pH 5.4) containing cysteine (1 mg/ml)).
7. The samples were rinsed 5 times in saline enriched by antibiotics.

What is claimed is:

1. A scaffold for use as growth supportive base for cells and tissue explants from three-dimensional tissue, comprising: a naturally occurring derived connective or skeletal tissue which has been treated for elimination of cellular and cytosolic elements comprising DNA, RNA, peptides, lipids and proteoglycans, and which has been grinded to form flakes having a size below 1000μ, which flakes are attached to each other, the scaffold having a porosity of at least 85%.

2. A scaffold according to claim 1, having at least 90% porosity.

3. A scaffold according to claim 2, having at least 95%–98% porosity.

4. A scaffold according to claim 1, where the naturally occurring connective or skeletal tissue is selected from the group consisting of: cartilage, epiphysis, perichondrium, periosteum, meniscus, ligaments, skin, demineralized bone and subinternal layer of intestine.

5. A scaffold according to claim 1, further comprising at least one compound selected from the group consisting of: adhesive molecules and growth factors.

6. A scaffold according to claim 5, wherein the adhesive molecules are selected from the group consisting of: integrines, proteoglycan, glycosaminoglycans, laminin, fibronectin, hyaluronic acid, polylysine and lysozyme.

7. A scaffold according to claim 5, wherein the growth factors are selected from the group consisting of: FGF's, TGF's, BMP's, and IGF's.

8. A scaffold according to claim 1, impregnated with cells forming a three-dimensional tissue.

9. A scaffold according to claim 8, wherein the three-dimensional tissue is composed of cells from autologous or allogeneic sources selected from the group consisting of: mesenchymal tissue, articular cartilage, epiphyseal tissue, perichondrial and periosteal flaps, skeletal tissue, liver and kidney tissues, neuronal tissue, dermis tissue and fibrous tissue, cells from an early embryonal stage, and stem progenitor cells from young and adult tissues.

10. A scaffold according to claim 1, wherein said three-dimensional tissue comprises epiphysial tissue.

11. A scaffold according to claim 10, wherein said epiphysial tissue is obtained from 17–22 week old fetus.

12. A prosthesis for implanting into a body of an individual comprising as an active ingredient the scaffold of claim 8.

13. A prosthesis for implanting into a body of an individual comprising as an active ingredient the scaffold of claim 9.

14. A prothesis according to claim 12, formed by at least 5 single-flake layers of the scaffold stacked on each other.

15. A prosthesis according to claim 14, wherein the edges of the layers are fused to each other, by thermo treatment.

16. A prosthesis according to claim 14, wherein the edges of the layers are fused to each other, by addition of adhesive molecules.

* * * * *

UNITED STATES PATENT AND TRADEMARK OFFICE
CERTIFICATE OF CORRECTION

PATENT NO. : 6,652,872 B2
DATED : November 25, 2003
INVENTOR(S) : Zvi Nevo et al.

It is certified that error appears in the above-identified patent and that said Letters Patent is hereby corrected as shown below:

<u>Title page,</u>
Item [73], "Ramat at" should read -- Ramot at --.

Signed and Sealed this

Twentieth Day of January, 2004

JON W. DUDAS
*Acting Director of the United States Patent and Trademark Office*